United States Patent [19]

Ward

[11] 4,183,937
[45] Jan. 15, 1980

[54] BLOOD PRESSURE LOWERING BENZOQUINOLIZINES

[75] Inventor: Terence J. Ward, Cippenham, England

[73] Assignee: John Wyeth & Brother Limited, Taplow, England

[21] Appl. No.: 962,823

[22] Filed: Nov. 22, 1978

[30] Foreign Application Priority Data

Dec. 14, 1977 [GB] United Kingdom ............... 52009/77

[51] Int. Cl.² ..................... A61K 31/47; C07D 455/06
[52] U.S. Cl. ......................................... 424/258; 546/95
[58] Field of Search ........................... 546/95; 424/258

[56] References Cited

U.S. PATENT DOCUMENTS

| | | | |
|---|---|---|---|
| 3,452,025 | 6/1969 | Hansen et al. | 546/95 |
| 3,634,431 | 1/1972 | Van Dyke | 546/95 |
| 4,076,820 | 2/1978 | Archibald et al. | 546/95 |

*Primary Examiner*—Alan L. Rotman
*Assistant Examiner*—Richard A. Schwartz
*Attorney, Agent, or Firm*—Arthur E. Wilfond

[57] ABSTRACT

The invention concerns novel benzoquinolizines of formula (I)

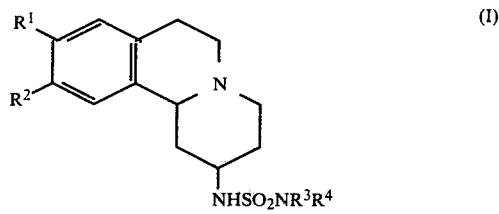

and their pharmaceutically acceptable acid addition salts. In formula (I) $R^1$ and $R^2$ which may be the same or different, each represent hydrogen, lower alkyl, lower alkoxy or halogen, $R^3$ and $R^4$ which may be the same or different each represent hydrogen, lower alkyl, aryl or aryl(lower)alkyl or $R^3$ and $R^4$ together represent a tetra- or penta-methylene chain.

The novel compounds of the invention lower blood pressure in warm-blooded animals.

9 Claims, No Drawings

BLOOD PRESSURE LOWERING BENZOQUINOLIZINES

The invention relates to novel heterocyclic compounds, more particularly to novel benzoquinolizines, to processes for preparing the compounds and to pharmaceutical compositions containing them.

The present invention provides novel benzoquinolizines of the general formula (I)

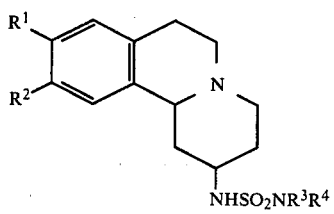

and the pharmaceutically acceptable acid addition salts thereof, wherein $R^1$ and $R^2$ which may be the same or different, each represent hydrogen, lower alkyl, lower alkoxy or halogen, $R^3$ and $R^4$ which may be the same or different each represent hydrogen, lower alkyl, aryl or aryl(lower)alkyl or $R^3$ and $R^4$ together represent a a tetra- or pentamethylene chain.

The term "lower" as used herein means that the radical referred to contains 1 to 6 carbon atoms. Preferably the radical contains 1 to 4 carbon atoms.

When a radical, or part of a radical, is referred to as "aryl" that radical or part of radical is preferably a phenyl or substituted phenyl group, The substituted phenyl group can be a phenyl group substituted by one or more substituents chosen from, for example, halogen (e.g. chlorine, fluorine or bromine), alkoxy (e.g. lower alkoxy such as methoxy or ethoxy), lower alkyl (e.g. methyl, ethyl, propyl or butyl), alkylenedioxy (e.g. methylenedioxy or ethylenedioxy), amino, lower alkylamino, diloweralkylamino or trifluoromethyl.

Examples of $R^1$ and $R^2$ are hydrogen, lower alkyl such as methyl, ethyl, propyl or butyl, lower alkoxy such as methoxy, ethoxy, propoxy or butoxy or halogen such as chlorine, fluorine or bromine. $R^1$ and $R^2$ can be different or the same, e.g. they both can be lower alkoxy or preferably hydrogen.

Examples of $R^3$ and $R^4$ are hydrogen, lower alkyl (e.g. methyl, ethyl, propyl or butyl), aryl (e.g. phenyl or substituted phenyl as mentioned above) or aryl(lower)alkyl (e.g. benzyl or phenethyl in which the phenyl ring can be substituted as mentioned above). When $R^3$ and $R^4$ together represent a tera- or pentamethylene chain the group $-NR^3R^4$ represents respectively a pyrrolidino or piperidino ring. Preferably $R^3$ and $R^4$ are both hydrogen.

The compounds of the invention may be prepared by a process in which an amine of general formula (II)

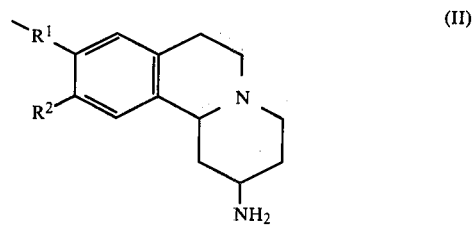

or an acid addition salt thereof (where $R^1$ and $R^2$ have the meanings given above) is reacted with a sulphonamide derivative of general formula (III)

$$NR^3R^4SO_2X \qquad (III)$$

where $R^3$ and $R^4$ are as defined above and X is amino or halo, preferably chloro. In a preferred process the amine of general formula (II) is reacted with a compound of formula (III) in which $R^3$ and $R^4$ are both hydrogen and X is amino. The latter compound is sulphamide. Starting compounds of formula (III) in which $R^3$ and $R^4$ are other than hydrogen can be prepared by reacting sulphamide with an appropriate amine of formula $NHR^{3'}R^{4'}$ [where $R^{3'}$ and $R^{4'}$ are lower alkyl, aryl or aryl(lower)alkyl or together represent a a tetra- or pentamethylene chain]. Compounds of formula (III) in which X is halo are known or can be made by methods known for analogous compounds. For example an isocyanate of general formula $R^{3'}NCO$ [where $R^{3'}$ is lower alkyl, aryl or aryl(lower)alkyl] may be reacted with fuming sulphuric acid to give an acid of formula $R^3NHSO_3H$ which may be halogenated with, for example, phosphorus trichloride, phosphorus pentachloride or thionyl chloride to the corresponding compound of general formula (III) in which X is halo.

The starting amines of general formula (II) are known compounds or they may be made by methods known for analogous compounds as, for example, described in our U.K. Specification No. 1,513,824.

The compounds of the invention may be prepared by an alternative process in which a compound of general formula (IV)

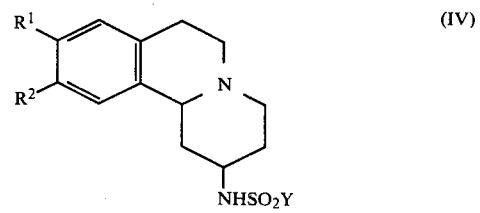

or an acid addition salt thereof, (wherein $R^1$ and $R^2$ have the meanings given above) and Y is chloro or bromo (preferably chloro) is reacted with a compound of general formula $NHR^3R^4$ (where $R^3$ and $R^4$ have the meanings given above). When $R^3$ and $R^4$ are both hydrogen the compound $NHR^3R^4$ is ammonia and when at least one of the groups $R^3R^4$ is other than hydrogen the compound is a primary or secondary amine. The starting compounds of general formula (IV) may be prepared by halogenating the corresponding acid of general formula (V)

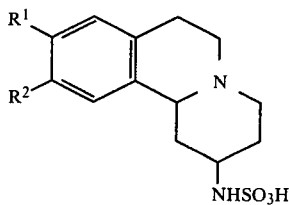

(V)

(where R¹ and R² have the meanings given above). The acid may be halogenated with a halogenating agent such as, for example, phosphorus trichloride, phosphorus pentachloride or thionyl chloride. The acid of general formula (V) may be prepared from an isocyanate of general formula (VI)

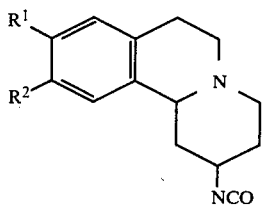

(VI)

(where R¹ and R² have the meanings given above) by treating it with fuming sulphuric acid. The isocyanate of general formula (VI) may be prepared from the amino of general formula (II), by for example, the methods disclosed in our U.K. Specification No. 1,513,824.

In a further process compounds of general formula (I) in which at least one of R³ and R⁴ is other than hydrogen may be prepared by reacting a compound of general formula (I) in which both R³ and R⁴ are hydrogen with a secondary or tertiary amine of general formula NHR³R⁴ (where R³ and R⁴ have the meanings given in connection with formula I except that at least one of R³ and R⁴ is other than hydrogen).

If necessary in the reactions hereinbefore described, reactive substituent groups may be protected during a reaction and the protecting group removed at a later stage. Once the compound of general formula (I) has been prepared then if necessary a substituent in the molecule may be converted into another substituent specified in connection with general formula (I).

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess two asymmetric carbon atoms and hence they can exist in various stereochemical forms. In addition they can exist as cis or trans isomers. It will be realised that if the starting material of formula (II) is a mixture of isomers the product of formula (I) will also be a mixture of isomers which can be separated, if required, by standard procedures. The preferred compounds of the invention are the trans isomers in which the —NHSO₂NR³R⁴ group is in the equatorial position i.e. compounds of the general formula (VI)

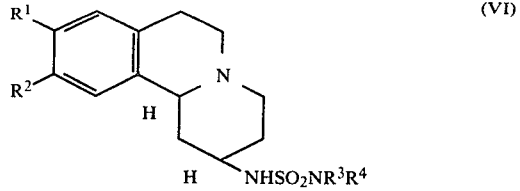

(VI)

and the pharmaceutically acceptable acid addition salts thereof (wherein R¹, R², R³ and R⁴ are as defined above). These compounds can be prepared by the methods described above starting from the corresponding trans isomer of general formula (II).

The compounds of the invention have blood pressure lowering activity. For example, the compounds exhibit antihypertensive activity upon administration to warm-blooded animals according to a standard pharmacological procedure. One such pharmacological test procedure is described below:

Female rats are rendered hypertensive by implanting subcutaneously two wax pellets (30 mg) containing desoxycorticosterone acetate (15 mg) followed immediately by uninephrectomy. The drinking water is replaced by normal saline ad lib for 4 weeks. Blood pressure stabilises at a hypertensive level after six weeks. Systolic pressure is measured indirectly before dosing with a test compound using an E and M pneumatic pulse transducer and a Devices MX2 recorder. Groups of 4 rats are dosed orally with suspensions or solution of the test compound in 0.5% hydroxypropylmethylcellulose 0.9% saline vehicle. Blood pressures are recorded again at 2, 6 and 24 hours and the results, expressed as a percentage of the pre-dose values compared with those of a similar group of rats receiving vehicle alone.

In the aforementioned test 2β-sulphonamido-1,2,3,4,6,7,11bα-hexahydro-2H-benzo[a]quinolizine, a representative compound of the present invention, was found to lower blood pressure by 47.7% 2 hours after dosing and by 50.3% 6 hours after dosing when administered at 50 mg/kg.

The invention further provides a pharmaceutical composition which comprises a compound of formula (I) or a pharmaceutically acceptable acid addition salt thereof, in association with a pharmaceutically acceptable carrier. In such a composition, the carrier may be a solid, liquid or mixture of a solid and a liquid. Solid form composition includes powders, tablets and capsules. A solid carrier can be one or more substances which may also act as flavouring agents, lubricants, solubilisers, suspending agents, binders or tablet disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter.

The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol containing from 10 to 75% of the glycol by weight is generally suitable.

In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from about 5 mg. to 500 mg., according to the particular need and the activity of the active ingredient. The invention also includes the compounds in the absence of carrier where the compounds are in unit dosage form.

The following Examples illustrated the invention.

EXAMPLE 1

2β-Sulphamamido-1,3,4,6,7,11bα-hexhydro-1H-benzo[a]quinolizine

To a solution of 2β-amino-1,3,4,6,7,11bα-hexahydro-2H-benzo[a]quinolizine (2.26 g.) in 1,2-dimethoxyethane (50 ml) was added sulphamide (1.344 g.) and the mixture was heated to reflux for 21 hours. The clear supernatent solution was decanted from a black tar and evaporated in vacuo. The residue was taken up in dichloromethane (25 ml) and quickly washed with water (2×15 ml). On standing for 0.5 hour, a precipitate formed from the organic layer, this was collected by filtration, washed with ice-cold dichloromethane and dried to give crude title compound (0.8 g.), m.p. 192°–193° C. A second crop of 0.1 g. was combined with the first.

A suspension of the title compound in ethanol was treated with ethanolic hydrogen chloride and shaken to solution. The solvent was evaporated and the product recrystallised from water to give the pure title compound as the hydrochloride, (0.71 g.), pale-brown plates, m.p. 205°–205.5° (dec). ($C_{13}H_{19}N_3O_2S$. HCl requires C, 48.14; H, 6.46; N, 13.47;. Found C, 48.48; H, 6.56; N, 13.28%).

EXAMPLE 2

9,10-Dimethoxy-2β-sulphamamido-1,3,4,6,7,11bα-hexahydro-2H-benzo[a]quinolizine

A slurry of 9,10-dimethoxy-2β-amino-1,3,4,6,7,11bα-hexahydro-2H-benzo[a]quinolizine (2.05 g.) in 1,2-dimethoxyethane (50 cm$^3$) with sulphamide (0.94 g) was stirred and heated to reflux for 21h. The clear solution was decanted from a small amount of red tar and evaporated in vacuo to an off-white glass-like solid. Crude title product was isolated as the hydrochloride, a very gummy yellow solid, re-converted to the free-base with aq.NaHCO$_3$, and extracted with CH$_2$Cl$_2$. Evaporation gave the crude base (1.22 g) as a yellow, glass-like solid. This was crystallised from a small volume of isopropanol overnight to give 9,10-dimethoxy-2β-sulphamamido-1,3,4,6,7,11bα-hexahydro-2H-benzo[a]quinolizine (0.48 g) as off-white micro-needles, m.p. 168°–172° C. (dec).

The product was slurried with hot ethanol (5 cm$^3$), acidified with ethanolic hydrogen chloride (1 cm$^3$), to give a clear solution and allowed to cool overnight. Filtration gave the title compound hydrochloride as a sticky pink solid which was triturated with hot MeOH-EtOH (1:1) with stirring, filtered and washed with ethanol to give title compound as hydrochloride hemihydrate (0.39 g), off-white spikes, m.p. 215°–217° C. (dec). ($C_{15}H_{23}N_3O_4S$.HCl. 0.5H$_2$O requires C, 46.57; H, 6.25; N, 10.86% Found: C, 46.40; H, 6.23; N, 10.63%)

EXAMPLE 3

N-[1,3,4,6,7,11bα-Hexahydro-2H-benzo[a]quinolizin-2β-yl]-N'-methylsulphamamide

Methyl isocyanate was converted to methanesulphamic acid with oleum and thence with PCl$_5$ to methanesulphamyl chloride by the method of J. A. Kloek and K. L. Leschinsky, J. Org. Chem. 41 (1976) 4028–9.

A slurry of the 2β-amino-1,3,4,6,7,11bα-hexahydro-2H-benzo[a]quinolizine dihydrochloride (2.75 g) and triethylamine (3.60 g) in dichloromethane (30 cm$^3$) was cooled to 0° C. and treated dropwise, with stirring, with a solution of methanesulphamyl chloride (95% pure; 1.30 g) in dichloromethane (10 cm$^3$). The mixture was stirred at room temperature for 10 hours and allowed to stand over the weekend. It was then washed with water (2×25 cm$^3$) and dried (MgSO$_4$). Filtration and evaporation afforded a brown, glass-like solid (2.24 g). The free base was chromatographed on silica and eluted with 10% ethanol in ethyl acetate to give the title compound as a pale-yellow solid (1.15 g). This was treated with ethanolic hydrogen chloride to give the hydrochloride of the title compound (0.82 g) as colourless crystals, m.p. 206.5°–208° C. (dec).

EXAMPLE 4

N,N-Dimethyl-N'-(1,3,4,6,7,11bα-hexahydro-2H-benzo[a]-quinolizin-2β-yl)sulphamamide A solution of dimethylsulphamyl chloride (1.44 g) in dichloromethane (15 cm$^3$) was added dropwise with stirring to an ice-cold solution of 2β-amino-1,3,4,6,7,11bα-hexahydro-2H-benzo[a]quinolizine (2.02 g) and triethylamine (1.01 g) in dichloromethane (15 cm$^3$). The mixture was allowed to stand at room temperature for 19 hours, then washed with water (2×25 cm³) and dried (MgSO₄). Filtration and evaporation afforded an oil which was taken up in ethanol and acidified with ethanolic hydrogen chloride. The mixture was allowed to stand in the refrigerator over the weekend, then stirred at room temperature to break up the precipitated crystals, filtered, and washed with ethanol to give the title compound as the hydrochloride (1.60 g) cream crystals, m.p. 201.5°–202.5° C. (dec).

EXAMPLE 5

N-(1,3,4,6,7,11bα-Hexahydro-2H-benzo[a]quinolizin-2β-yl)-N'-phenylsulphamamide

A solution of phenylsulphamoyl chloride (prepared in two steps from aniline by method of J. A. Kloek & K. L. Leschinsky, J. O. C., (1976), 41, 4028–9); (1.12 g) in dichloromethane (10 cm³) was added to a stirred ice-cold solution of 2β-amino-1,3,4,6,7,11bα-hexahydro-2H-benzo[a]quinolizine (1.25 g) and triethylamine (3 g) in dichloromethane (20 cm³). The mixture was allowed to stand at room temperature for 90 hours, then washed with water (2×25 cm³) and dried (MgSO₄). Filtration and evaporation afforded a glass-like solid (2.32 g). Repeated solution and evaporation in a variety of solvents converted this into a pale-brown crystalline solid, which was triturated with benzene (10 cm³) and filtered to give the crude product as its base (2.0 g). This was dissolved in ethanol (6 cm³), acidified with ethanolic hydrogen chloride, the solvent evaporated and the residue crystallised overnight from methanol. Ethanol was added, and the methanol evaporated on the rotary evaporator. Three crops of the crude hydrochloride were collected by filtration over a period of three days. These were combined, dissolved in methanol, diluted with ethanol, the methanol evaporated on the rotary evaporator, and the residual suspension in ethanol stirred and heated to reflux for 2 hours. After cooling in ice, the precipitate was collected by filtration. Concentration of the mother-liquors gave a second crop and, after standing three days, a large third crop. All crops (possessing similar melting points) were combined and washed with ice-cold ethanol, to give pure title compound as the hydrochloride hemihydrate (0.41 g), cream crystals, m.p. 210°–213° C. (dec.).

EXAMPLE 6

N-(1,3,4,6,7,11bα-Hexahydro-2H-benzo[a]quinolizin-2β-aminosulphonyl)pyrrollidine A solution of pyrollidinesulphonyl chloride (2.0 g) in dichloromethane (5 cm³) was added dropwise, with stirring, to an ice-cold solution of 2β-amino-1,3,4,6,7,11bα-hexahydro-2H-benzo[a]quinolizine (2.02 g) and triethylamine (1.25 g) in dichloromethane (20 cm³). The clear solution was stirred for a further ¼ hour, then allowed to stand at room temperature for 45 hours. The turbid mixture was washed with water (2×25 cm³) and dried (MgSO₄). Filtration and evaporation afforded a brown gum (3.67 g), which was dissolved in hot ethanol (10 cm³), acidified with ethanolic hydrogen chloride, evaporated, the residue taken up in a small volume of ethanol and scratched, to give the crude product as its hydrochloride. This was recrystallised twice from ethanol to give pure title compound as the hydrochloride hemihydrate (1.30 g), very pale yellow rods, m.p. 206°–207° C. (dec).

EXAMPLE 7

N,N-Diethyl-N'-(1,3,4,6,7,11bα-hexahydro-2H-benzo[a]quinolizin-2β-yl)sulphamamide A solution of diethylaminesulphonyl chloride (prepared from diethylamine and thionyl chloride; 2.0 g) in dichloromethane (5 cm³) was added dropwise, with stirring, to an ice-cold solution of 2β-amino-1,3,4,6,7,11bα-hexahydro-2H-benzo[a]quinolizine (2.02 g) and triethylamine (1.25 g) in dichloromethane (20 cm³). The clear solution was stirred for 15 min., then allowed to stand at room temperature for 45 hours, during which time precipitation occurred. The mixture was washed with water (2×25 cm³) and the clear organic layer dried (MgSO₄). Filtration and evaporation afforded a brown gum (3.38 g), which was chromatographed on silica eluted with 10% ethanol in ethyl acetate to give the crude product as its base, a brown oil (2.01 g). This was converted to the hydrochloride with ethanolic hydrogen chloride. Very slow precipitation (several days) from iso-propanol gave, in three crops, pure title compound as the hydrochloride quaterhydrate (0.80 g), colourless glass, m.p. 120°–140° C.

I claim:

1. A compound selected from the group consisting of a benzoquinolizine of the formula (I)

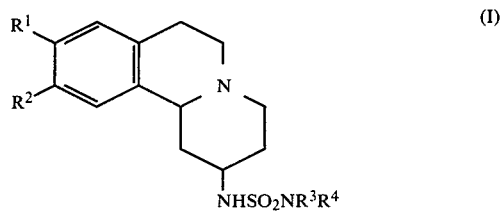

and a pharmaceutically acceptable acid addition salt thereof, wherein $R^1$ and $R^2$ which may be the same or different, each represent hydrogen, lower alkyl, lower alkoxy or halogen, $R^3$ and $R^4$ which may be the same or different each represent hydrogen, lower alkyl, phenyl, phenyl loweralkyl, substituted phenyl or substituted phenyl loweralkyl, wherein the phenyl substituents are selected from one or more of halogen, lower alkoxy, lower alkyl, lower alkylenedioxy, amino, lower alkylamino, diloweralkyl amino or trifluoromethyl or $R^3$ and $R^4$ together represent a a tetra- or pentamethylene chain.

2. A compound according to claim 1 which is 2β-sulphamamido-1,3,4,6,7,11bα-hexahydro-2H-benzo[a]quinolizine or a pharmaceutically acceptable salt thereof.

3. A compound according to claim 1 which is 9,10-dimethoxy-2β-sulphamamido-1,3,4,6,7,11bα-hexahydro-2H-benzo[a]quinolizine or a pharmaceutically acceptable salt thereof.

4. A compound according to claim 1 which is N-[1,3,4,6,7,11bα-hexahydro-2H-benzo[a]quinolizin-2β-yl]-N'-methylsulphamamide or a pharmaceutically acceptable salt thereof.

5. A compound according to claim 1 which is N,N-dimethyl-N'-(1,3,4,6,7,11bα-hexahydro-2H-benzo[a]quinolizin-2β-yl)sulphamamide or a pharmaceutically acceptable salt thereof.

6. A compound according to claim 1 which is N-(1,3,4,6,7,11bα-hexahydro-2H-benzo[a]quinolizin-2β-yl)-N'-phenylsulphamamide.

7. A compound according to claim 1 which is N-(1,3,4,6,7,11bα-hexahydro-2H-benzo[a]quinolizin-2β-aminosulphonyl)pyrrollidine.

8. A compound according to claim 1 which is N,N-diethyl-N'-(1,3,4,6,7,11bα-hexahydro-2H-benzo[a]-quinolizin-2β-yl)sulphamamide.

9. A pharmaceutical composition having blood pressure lowering activity comprising an blood pressure lowering amount of a compound selected from the group consisting of a benzoquinolizine of the formula (I)

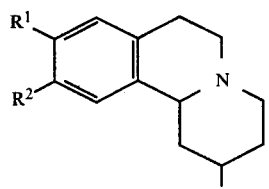

and a pharmaceutically acceptable acid addition salt thereof, wherein $R^1$ and $R^2$ which may be the same or different, each represent hydrogen, lower alkyl, lower alkoxy or halogen, $R^3$ and $R^4$ which may be the same or different each represent hydrogen, lower alkyl, phenyl, phenyl loweralkyl, substituted phenyl or substituted phenyl loweralkyl, wherein the phenyl substituents are selected from one or more of halogen, lower alkoxy, lower alkyl, lower alkylenedioxy, amino, lower alkylamino, diloweralkyl amino or trifluoromethyl or $R^3$ and $R^4$ together represent a a tetra- or pentamethylene chain, in association with a pharmaceutically acceptable carrier.

* * * * *